(12) United States Patent
Feldman

(10) Patent No.: US 7,832,043 B1
(45) Date of Patent: Nov. 16, 2010

(54) TOOTHBRUSH

(76) Inventor: Yasha Feldman, 255 Vandalia Ave., Apt. 9H, Brooklyn, NY (US) 11239-1413

(*) Notice: Subject to any disclaimer, the term of this patent is extended or adjusted under 35 U.S.C. 154(b) by 0 days.

(21) Appl. No.: 12/461,631

(22) Filed: Aug. 19, 2009

(51) Int. Cl.
*A46B 13/02* (2006.01)
*A61C 17/26* (2006.01)

(52) U.S. Cl. .................... 15/28; 15/29; 15/167.2

(58) Field of Classification Search ............ 15/167.2, 15/23, 28, 29; 401/9, 10, 11
See application file for complete search history.

(56) References Cited

U.S. PATENT DOCUMENTS

| | | | | |
|---|---|---|---|---|
| 1,189,505 A | * | 7/1916 | Stockton | 401/10 |
| 1,586,262 A | * | 5/1926 | Noble | 401/10 |
| 1,616,484 A | * | 2/1927 | Beynon | 15/167.2 |
| 1,647,393 A | * | 11/1927 | Carek | 15/36 |
| 2,588,601 A | * | 3/1952 | Zavagno | 15/167.2 |
| 2,701,380 A | * | 2/1955 | Ripper | 15/167.2 |
| 3,440,680 A | * | 4/1969 | Werding | 15/321 |
| 3,535,047 A | * | 10/1970 | Vireno | 401/10 |
| 3,732,589 A | * | 5/1973 | Burki | 15/22.1 |
| 3,925,841 A | * | 12/1975 | Caliendo | 15/23 |
| 4,155,663 A | * | 5/1979 | Cerquozzi | 401/135 |
| 4,176,980 A | * | 12/1979 | O'Neal et al. | 401/162 |
| 5,337,435 A | * | 8/1994 | Krasner et al. | 15/23 |
| 6,343,396 B1 | * | 2/2002 | Simovitz et al. | 15/27 |

* cited by examiner

*Primary Examiner*—Randall Chin
(74) *Attorney, Agent, or Firm*—I. Zborovsky

(57) ABSTRACT

A toothbrush has a body, and a brush member connected to the body, the brush member including three brushes which are arranged at an angle relative to one another so as to provide two side brushes and one intermediate brush extending between the side brushes and to form an elongated passage between the brushes, adapted to receive teeth so that the brushes can contact the teeth from an inner side, from an outer side, and from a biting surface.

7 Claims, 5 Drawing Sheets

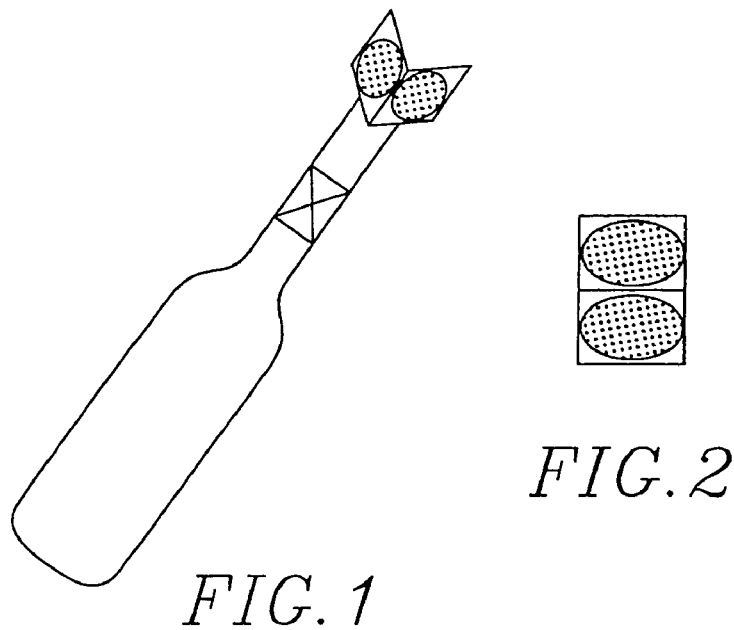
FIG. 1
FIG. 2
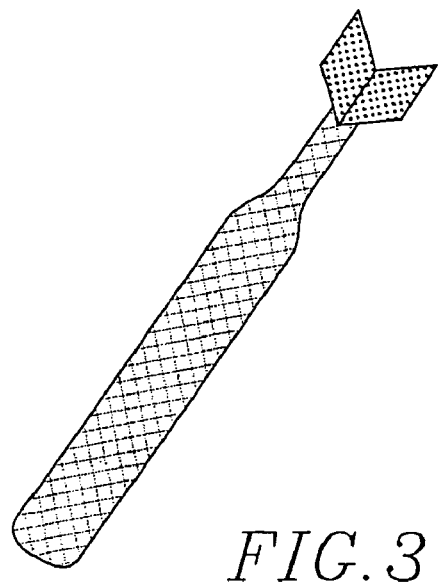
FIG. 3

MICROCOMPRESSOR
FOR AIR SUPPLY

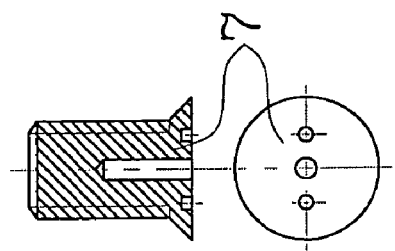
FIG. 10
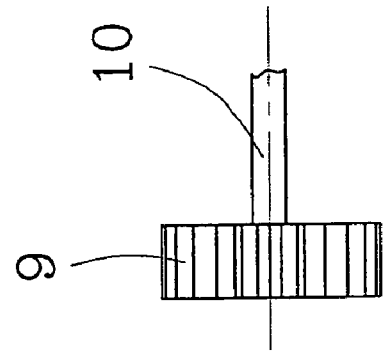
FIG. 12
FIG. 11
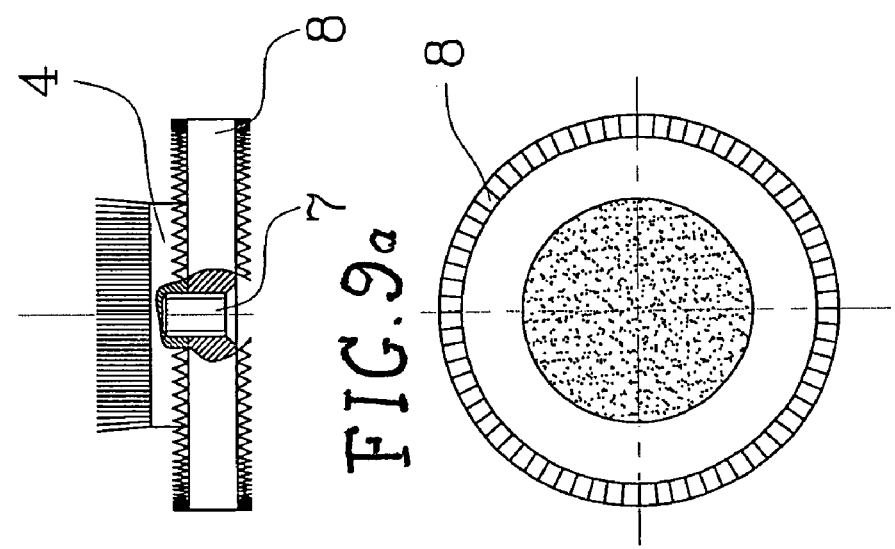
FIG. 9a
FIG. 9

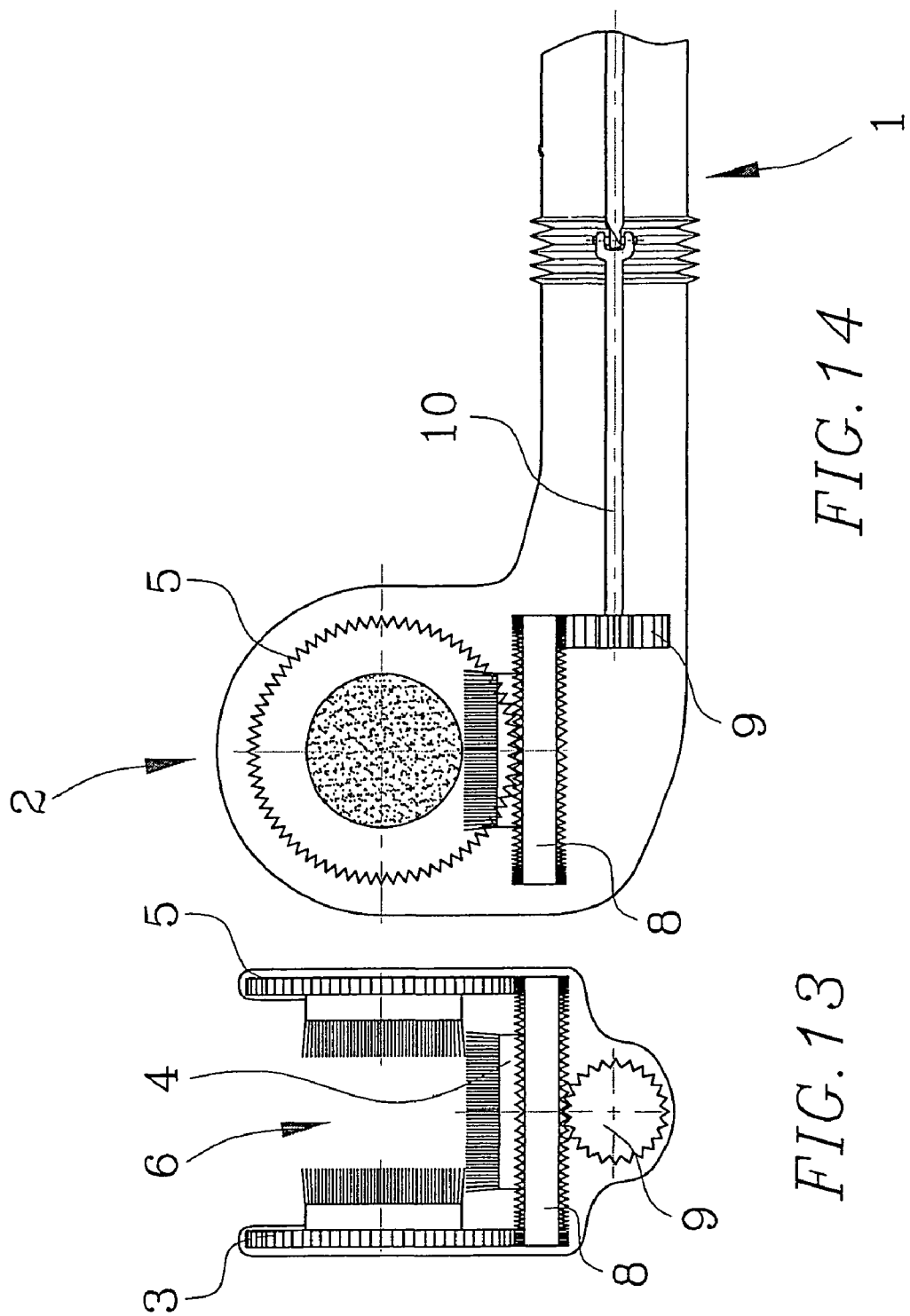

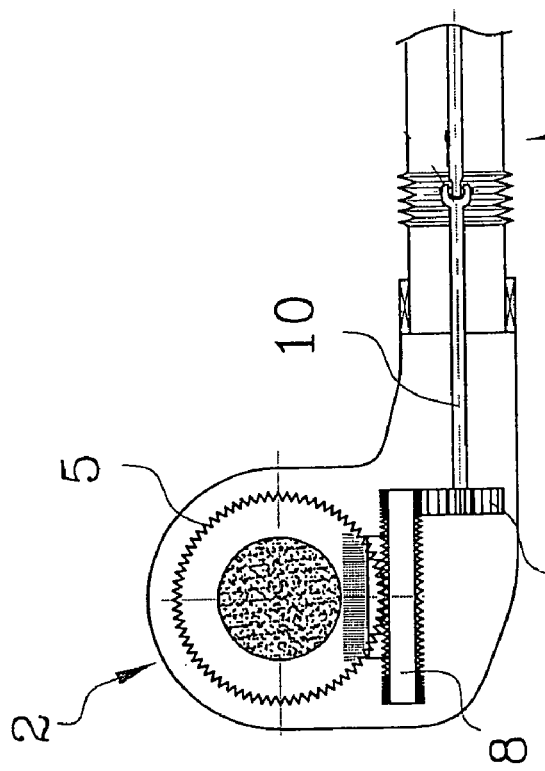
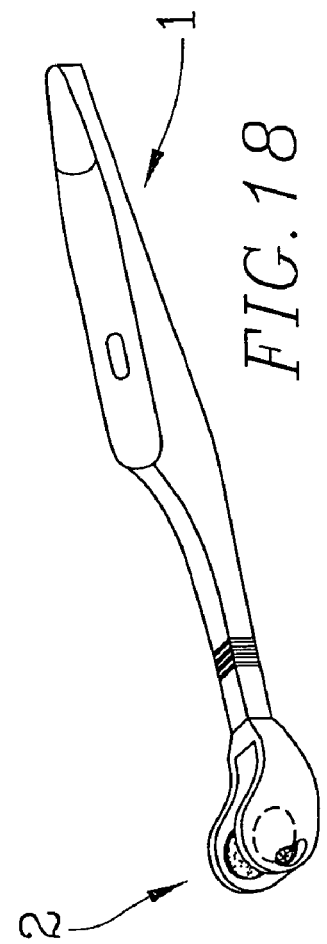
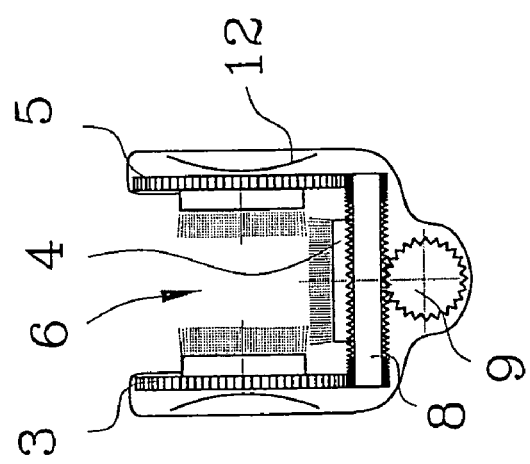
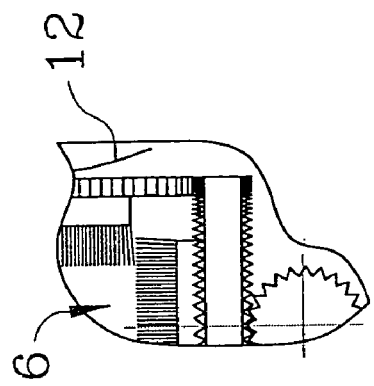

TOOTHBRUSH

BACKGROUND OF THE INVENTION

The present invention relates to toothbrushes.

Toothbrushes are well known in many modifications. It is believed that it is always desirable to provide a new toothbrush which is a further improvement of the existing toothbrushes.

SUMMARY OF THE INVENTION

Accordingly, it is an object of the present invention to provide a new toothbrush, which is a further improvement of the existing toothbrushes.

In keeping with these objects and with others which will become apparent hereinafter, one feature of the present invention resides, briefly stated, in a toothbrush which has a body, and a brush part including three rotatable brushes with two lateral brushes and one bottom brush forming a space therebetween; and means for rotating said brushes of said brush part.

When the toothbrush is designed in accordance with the present invention, it provides a further improvement of cleaning teeth simultaneously from three sides, gaps between the teeth are ventilated by means of air, gums are massaged, tongue can be cleaned from impurities, etc.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a plan view of a toothbrush in accordance with the present invention;

FIG. 2 is a perspective view of the toothbrush in accordance with the present invention;

FIG. 3 is a view showing a brush part of the inventive toothbrush;

FIGS. 9a and 9b are a side view and an end view for attaching the brush of the inventive toothbrush;

FIG. 10 is a side view and a bottom view of an attaching pin;

FIGS. 11 and 12 are an end view and a side view of a part of the drive of the inventive toothbrush;

FIGS. 13 and 14 is an end view and a side view of a working part of the toothbrush in accordance with the present invention;

FIGS. 15 and 16 are two further views showing another modification of the brush member of the inventive toothbrush;

FIG. 17 is a view showing the toothbrush in accordance with the present invention with a replaceable brush part; and FIG. 18 is a perspective view of the toothbrush in accordance with the present invention.

DESCRIPTION OF THE PREFERRED EMBODIMENTS

Figure 4:
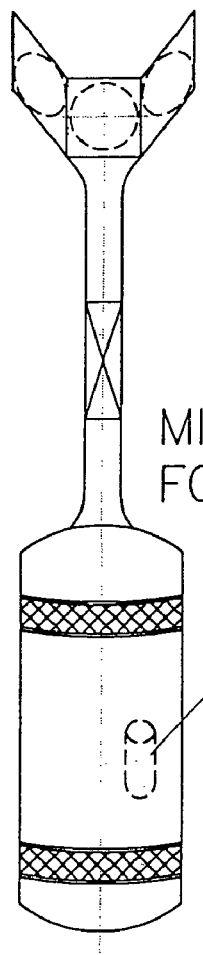
FIG. 4 is another view of the toothbrush in accordance with the present invention.

A new toothbrush in accordance with the present invention has a body which is identified as a whole with reference numeral 1 and a brush part connected with the body and identified as a whole with reference numeral 2. The brush part includes three brushes 3, 4 and 5 which are located at an angle relative to on another, preferably an angle of 90°, so as to form a longitudinal channel 6 therebetween.

The brushes 3, 4, 5 and the channel 6 therebetween are configured so that the brushes can contact teeth from three sides, namely from the biting side, from the front side and from the rear side.

Figure 5:
FIGS. 5, 6 and 7 are views showing brushes with bristles in the toothbrush.
Figure 6:
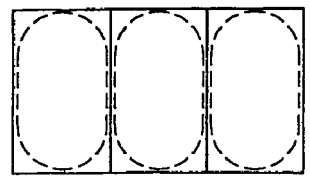
Figure 7:
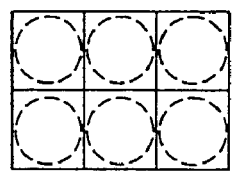

FIGS. 5, 6 and 7 show the shapes and possible locations of the brushes with bristles in the body of the toothbrush.

Figure 8:
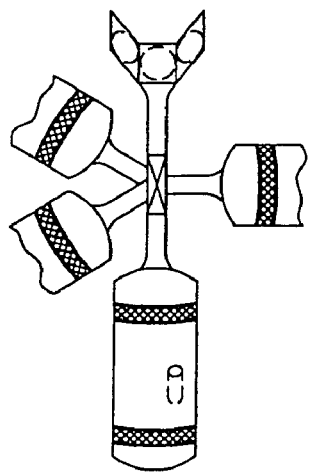
FIG. 8 is a view showing different positions of the brushes of the inventive toothbrush for better outcome.

As can be seen from FIG. 8, the brushes can change their position for better action on the teeth, so that one of a plurality of the positions shown in FIG. 8 can be assumed for the brushing process.

For this purpose, the brush part 2 of the inventive toothbrush is turnable relative to the body 1 of the brush.

The body 1 of the brush is formed so that it accommodates mechanical and electrical systems of power supply, and also forms a container for a toothpaste and its supply to the teeth.

As can be seen from FIGS. 7-10, the intermediate brush 4 can be connected by a pin 7 having openings for a key, to a gear 8 provided with teeth on its opposite sides. The side brushes 3 and 5 are provided with lateral teeth which are in engagement with upper teeth of the gear 8. The lower teeth of the gear 8 are engaged with a pinion 9 which is turnable by a shaft 10, which extends in a tubular passage and is driven in rotation by a not shown drive located in the body of the toothbrush the toothbrush can be battery-operated or operated from an outside power supply.

When the drive of the toothbrush is activated and the shaft 5 is rotated, the pinion 9 rotates the gear 8, and the brushes 2, 3, and 4 are rotated, thus cleaning the teeth from their inner side, their outer side, and their biting surface.

The toothbrush thus improves cleaning of teeth, massaging of gums, cleaning of a tongue, cleaning gaps between the teeth by means of air, etc.

FIG. 11 identifies a hinge which allows turning of the brush parts 2 of the toothbrush relative to the body 1 of the toothbrush. It is to be understood that parts of the drive are also turnable relative to one another, for example by means of a cardan joint in the middle of a transmission shaft, to allow turning of the brush part 2 relative to the body 1.

The brush can be provided with air passage and a miniature fan for blowing air into the gap between the brushes 2, 3, 4. Also, a passage can be provided for supplying a toothpaste into the passage 6 between the brushes 2, 3, 4.

As shown in FIGS. 15 and 16 the side brushes 2 and 4 can be arranged movably in a transverse direction, and springs 12 can be provided for biasing these brushes in the transverse direction.

As shown in FIG. 17, the brush part 2 can be connected with the body 1 detachably, by known means for example by clamps, pins, etc. When necessary the brush part 2 can be removed from the body 1 for cleaning purposes.

The invention claimed is:

1. A toothbrush, comprising a body; a brush member connected to said body, said brush member including three brushes which are arranged at an angle relative to one another so as to provide two side brushes and one intermediate brush extending between said side brushes and to form an elongated passage between said brushes, adapted to receive teeth so that said brushes can contact the teeth from an inner side, from an outer side and from a biting surface, said brushes of said brush member being rotatable; means for rotating said brushes of said brush member and including a gear having two opposite surfaces with teeth provided on one of said surfaces of said gear and engaging with teeth of said intermediate brush and with teeth of said side brushes, while the other of said surfaces of said gear has a plurality of teeth engageable with teeth on a drive element for rotation of said gear having said two opposite surfaces.

2. A toothbrush as defined in claim 1, wherein said side brushes are movable in a transverse direction transversely to said intermediate brush; and further comprising spring means which spring-bias only said side brushes in the transverse direction toward said elongated passage.

3. A toothbrush as defined in claim 1, wherein said side brushes extend perpendicularly to said intermediate brush, wherein said teeth of said side brushes extend perpendicular to said teeth of said intermediate brush, wherein said teeth of said one surface of said gear having two opposite surfaces engages with said teeth of said intermediate brush provided on a face surface of said intermediate brush, wherein said teeth on said one surface of said gear with two opposite surfaces engages with the teeth of said side brushes on a periphery of said side brushes.

4. A toothbrush as defined in claim 1, wherein said brush member is connected detachably with said body; and further comprising means for attachably connecting said brush member with said body.

5. A toothbrush as defined in claim 1; and further comprising means for supplying air into said passage formed by said brushes.

6. A toothbrush as defined in claim 1; and further comprising means for supplying a toothpaste in said passage between said brushes.

7. A toothbrush as defined in claim 1; and further comprising means for removably connecting said intermediate brush of said brush member with said gear having two opposite surfaces.

* * * * *